United States Patent [19]

Stadler et al.

[11] 3,989,739

[45] Nov. 2, 1976

[54] OXYGENATED DECALIN DERIVATIVES

[75] Inventors: Paul A. Stadler, Biel-Benken; Albert Eschenmoser, Kusnacht, Zurich; Erling Sundt, Pinchat-Geneva, all of Switzerland

[73] Assignee: Firmenich S.A., Geneva, Switzerland

[22] Filed: Jan. 11, 1974

[21] Appl. No.: 432,643

Related U.S. Application Data

[62] Division of Ser. No. 316,071, Dec. 18, 1972, abandoned, which is a division of Ser. No. 780,162, Nov. 29, 1968, abandoned.

[30] Foreign Application Priority Data

Nov. 29, 1967 Switzerland..................... 16745/67
Nov. 22, 1968 Switzerland..................... 17405/68

[52] U.S. Cl. ........................... 260/486 R; 252/522; 260/488 B; 260/586 F; 260/586 P; 260/611 F

[51] Int. Cl.$^2$.................. C07C 69/06; C07C 69/14; C07C 69/24; C07C 69/52; C07C 69/54

[58] Field of Search.......... 260/488 B, 486 R, 617 F

[56] References Cited
FOREIGN PATENTS OR APPLICATIONS
1,593,814   7/1970   France ........................... 260/488 B OTHER PUBLICATIONS
Chem. Abstracts, 55; 2724d (1961).

*Primary Examiner*—Vivian Garner
*Attorney, Agent, or Firm*—Pennie & Edmonds

[57] ABSTRACT

Oxygenated decalin derivatives, the use thereof as fragrances or odor-modifying agents, and methods for preparing the said derivatives.

2 Claims, No Drawings

OXYGENATED DECALIN DERIVATIVES

REFERENCE TO RELATED APPLICATIONS

This is a division of application Ser. No. 316,071, filed Dec. 18, 1972, now abandoned, which is a division of copending U.S. application Ser. No. 780,162, filed Nov. 29, 1968, now abandoned.

The present invention relates to oxygenated decalin derivatives of formula

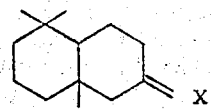

wherein X represents either oxygen or two monovalent radicals one of them being hydrogen, the other one being a radical of formula

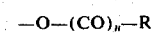

wherein R represents hydrogen, or a saturated linear or branched aliphatic radical comprising 1 to 6 carbon atoms or an unsaturated linear or branched aliphatic radical comprising 2 to 6 carbon atoms and $n$ is 0 or 1. The invention also relates to processes for the manufacture of compounds I and to their use as fragrant ingredients in perfume compositions and perfumed products.

The invention relates more particularly to compounds of formulae

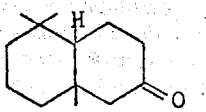

and

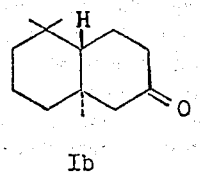

which represent the cis- and trans-isomers respectively of the compound of formula I wherein X represents oxygen.

The invention relates also more particularly to compounds of formulae

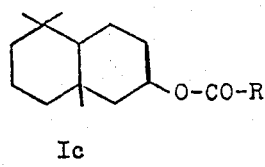

and

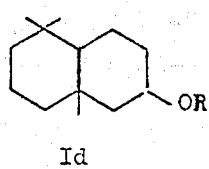

wherein R has the same meaning as above. In the above formulae I, Ic and Id, R represents radicals such as for instance methyl, ethyl, butyl, amyl, hexyl, isopropyl, isobutyl, sec.-butyl, tert.-butyl, 3-methylbutyl, 1-methylbutyl, 2-methylbutyl, neopentyl, 1-ethylpropyl, 1,2-dimethylpropyl, tert.-amyl, isohexyl, 1-methylpentyl, 2-methylpentyl, 3-methylpentyl, 4-methylpentyl, 1-ethylbutyl, 2-ethylbutyl, vinyl, propenyl, allyl, isopropenyl, butenyl, 2-butenyl, 3-butenyl, isobutenyl, 2-isobutenyl, 1-methylpropenyl, ethylvinyl, α-methylallyl, isopentenyl, 3-dimethylallyl, 3-methyl-3-butenyl, 1-methylbutenyl, 1-propylvinyl, 1-methyl-2-butenyl, 1-methyl-3-butenyl, 2-methylbutenyl, 2-ethylallyl, 2-methyl-2-butenyl, 2-methyl-3-butenyl, 1-ethylpropenyl, 1-ethylallyl, 1-dimethylallyl, trimethylvinyl, 1-isopropylvinyl, 1,2-dimethylallyl, butadienyl, butadien-2-yl, isopentadienyl, 1-methylbutadienyl, 1,4-pentadien-2-yl, 1,3-pentadien-2-yl, 1,4-pentadien-2-yl, 2-methylbutadienyl, 2-vinylallyl, 1-vinylpropenyl, divinylmethyl, 2-propynyl, 2-butynyl, 3-butynyl, 1-methyl-2-propynyl, 1-methyl-2-butynyl, 1-methyl-3-butynyl, 2-methyl-3-butynyl, 1-ethyl-2-propynyl radicals.

It has been found that the decalin derivatives Ia, Ib, Ic and Id, except the compound Id wherein R is hydrogen, have particularly interesting and valuable fragrant properties and, consequently, are useful as fragrant ingredients in the perfume industry. In particular, the said compounds can be used as odoriferous ingredients in concentrated or diluted perfumes and in perfumed products such as soaps, detergents, cosmetics, waxes and other products which may be perfumed to make them commercially more attractive. The above compounds are capable of imparting to perfume compositions an appreciated woody odour which is very tenacious particularly in the case of compounds Ic. The ketones Ia and Ib possess in addition an appreciated amber-like character while their woody character differs somewhat from that of the other compounds. Generally speaking the compounds Ia, Ib, Ic and Id are particularly effective when added to perfumes of oriental types to which they impart a very natural richness of a distinctive type.

The proportions in which the new decalin derivatives can be used to produce desirable odoriferous effects vary within rather wide limits and depend on the type of product to which they are added. In the preparation of perfume compositions, for instance, interesting effects can be obtained with proportions of 0.1 to 10% of the said derivatives, based on the total weight of the composition. When the new derivatives are used in perfumed products in combination with other fragrant substances, the proportions of the said derivatives can amount to 10 to 5000 ppm of the total weight of the product. In other cases, for instance in the preparation of concentrates or modifiers which will ultimately be diluted with solvents or mixed with other fragrant substances before use or which serve as perfume bases, the concentration of the said ketones can be higher than 10%, for instance 15% or even higher.

The proportions given hereinbefore are illustrative only and not absolute values. It is understood that other concentrations may be used depending on the specific odoriferous effects to be developed.

According to the invention the esters of formula

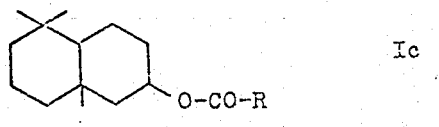

(formula I, X = H plus —OCOR) wherein R has the meaning defined above, are obtained by esterifying a carbinol of formula Id wherein R is H, with an acylating agent of formula R—COX (II) wherein R has the meaning defined above and X represents an easily removable leaving group.

The esterification can be carried out by conventional methods usually used for acylating alcohols (see for example D. J. Cram and G. S. Hammond, Organic Chemistry, McGraw-Hill Inc. New York (1959) p. 310 and following), for example by means of acylating agents II wherein X is a halogen, e.g. chlorine or bromine, or a tosylate group, or the group R—COO— wherein R has the meaning defined above. The esterification is conveniently carried out in the presence of a neutralising agent capable of binding the acid formed in the esterification, e.g. in the presence of an organic base such as triethylamine. A preferred method consists in using an anhydride in the presence of pyridine.

According to the invention the esters of formula Ic are also obtained by reacting 6,10-dimethyl-1,5,9-undecatriene IV with a mixture of a mineral acid and an organic acid of formula R—COOH wherein R has the meaning defined above. Examples of suitable mineral acids are sulphuric acid, phosphoric acid, perchloric acid and hydrochloric acid.

According to the invention the ketones Ia and Ib are prepared by a process which comprises oxidising 1,7,7-trimethyl-bicyclo[4.4.0]decan-3-ol by means of an oxidising agent. The above oxidation can be carried out by usual means, for instance by means of silver carbonate in the presence of diatomaceous earth or by means of oxidised derivatives of certain transition elements such as chromium and copper [see for instance, Organic Chemistry by D. J. Cram and G. S. Hammond, pp. 432–436, McGraw-Hill, New York (1959)]. The oxidation can also be performed by means of a ketone in the presence of an aluminum alkoxide according to the method of Oppenauer. Ketones suitable for the above oxidation are acetone, cyclohexanone, diethylketone, methylethylketone and methylhexylketone. Suitable alkoxides include aluminum butoxide, isobutoxide and isopropoxide. The oxidation is preferably carried out by means of either $CrO_3$ or methylethylketone in the presence of aluminum isopropoxide.

The ketones resulting from the oxidation of the above mentioned carbinol consists of a mixture of the cis- and trans-isomers Ia and Ib respectively. Crystallisation of this mixture by usual means affords the solid cis-isomer in pure form. The liquid trans-isomer is then separated from the crystallisation mother-liquors by preparative vapour phase chromatography according to usual procedures. Both isomers have similar odoriferous properties, the trans-isomer having a slightly more camphor-like odour than the cis-isomer. When desired, they can be used separately in the perfume industry. However, in practice it is more economic to use the mixture of the cis- and trans-isomeric ketones as an odoriferous ingredient.

The ethers of formula Id are prepared, according to the invention, by etherifying the carbinol of formula Id wherein R represents hydrogen, with an alkylating agent of formula RX(III) wherein R has the meaning defined above and X represents an easily removable leaving group. The above etherification can be carried out by conventional methods [see for instance D. J. Cram and G. S. Hammond, Organic Chemistry, McGraw-Hill, New York (1959) p. 207 and following]. For example the etherification can be carried out by means of agents III wherein X represents a halogen, e.g. bromine or iodine, or a tosylate group. The etherification is preferably performed in the presence of alkali, in order to convert the alcohol to alcoholate prior to its reaction with the alkylating agent. Alkalis such as NaOH or KOH, or the corresponding alkali metals themselves can be employed. It must be understood that the examples of etherification given above are not limitative; other common etherification processes can also be convenient.

The carbinol of formula Id wherein R represents hydrogen used in the preparation of the ketones Ia and Ib can be prepared for instance by saponifying esters of formula Ic. The saponification can be carried out according to conventional methods, for instance by means of alkalis, e.g. KOH, NaOH and LiOH, in the presence of aqueous alcohols such as methanol or amyl alcohol.

The 6,10-dimethyl-1,5,9-undecatriene (IV) used as an intermediate in one of the processes for preparing the esters Ic can be obtained by reacting a geranyl halide V, e.g. the chloride or bromide, with an allyl halide VI, e.g. the chloride or bromide, under usual Grignard reaction conditions.

The preparation of the ketones Ia and Ib, the esters Ic and the various intermediates is summarised in the following reaction diagram wherein X represents halogen.

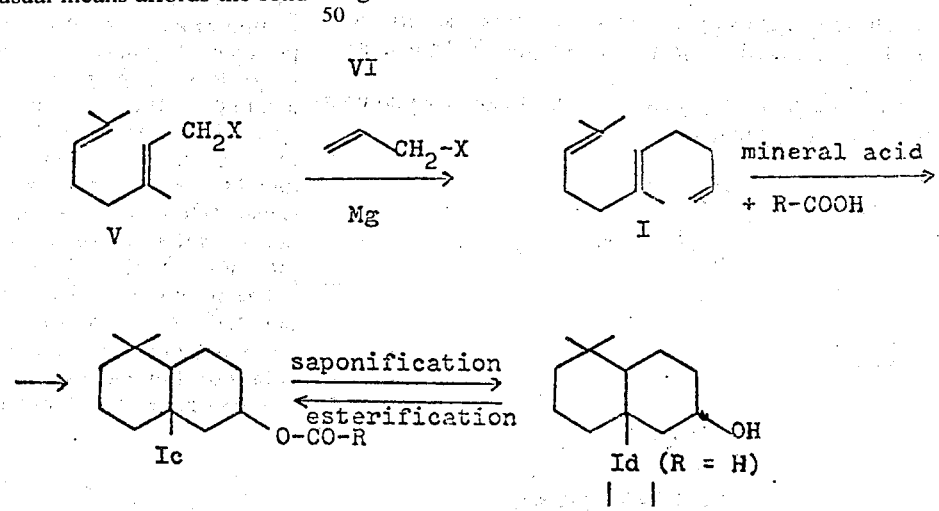

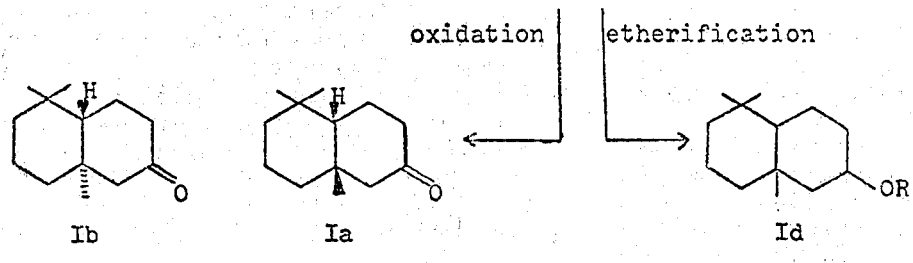

The invention is further illustrated in a more detailed manner by the following Examples wherein the temperatures are indicated in degrees Centigrade.

EXAMPLE 1

Perfume Composition of the "Chypre" Type

A perfume composition of the "Chypre" type was prepared by mixing together the following ingredients (parts by weight):

| | |
|---|---|
| Undecenal at 10% * | 10 |
| Dodecanal at 10% * | 20 |
| Synthetic Rose | 60 |
| Synthetic Jasmine | 120 |
| Hydroxycitronellal | 30 |
| Isojasmone | 5 |
| γ-Methylionone | 90 |
| Resinoid of styrax, at 50% * | 60 |
| Cinnamyl alcohol | 15 |
| Bergamot | 45 |
| Celery at 10% * | 70 |
| Citral at 10% * | 30 |
| Patchouli | 100 |
| Santal oriental | 20 |
| Vetyver Bourbon | 40 |
| Cedryl acetate | 15 |
| Oak moss absolute, at 50% * | 40 |
| Oil of myrrh | 20 |
| Labdanum cyst absolute, at 10% * | 20 |
| Degreased natural civet, at 10% * | 20 |
| Musk ketone 60 | |
| Coumarin | 30 |
| Ethylvanillin | 15 |
| Jasmine absolute | 10 |
| Bulgarian rose oil | 5 |
| Total | 950 |

* In diethyl phthalate

By adding to 950 g. of this blend 50 g. of an approximately 1 : 1 mixture of cis- and trans-1,7,7-trimethylbicyclo[4.4.0]decan-3-ones, the composition obtained had a pleasant amber and woody note which had a very natural touch.

EXAMPLE 2

Perfume Composition of the "Floral-Chypre" Type

A "Floral-Chypre" perfume composition was prepared by mixing together the following ingredients (parts by weight):

| | |
|---|---|
| Decanal at 10% * | 5 |
| Undecenal at 10% * | 45 |
| Dodecanal at 10% * | 10 |
| Synthetic Lily of the Valley | 150 |
| Synthetic Rose oil | 150 |
| Synthetic Jasmine | 90 |
| Synthetic Carnation | 60 |
| Bergamot | 90 |

-continued

| | |
|---|---|
| Ylang extra | 45 |
| Tarragon at 10% * | 30 |
| Oak moss absolute, at 50% * | 30 |
| Labdanum cyst absolute at 10% * | 20 |
| Benzoin tears, at 10% * | 10 |
| Degreased natural civet, at 10% * | 15 |
| γ-Methylionone | 60 |
| Patchouli | 5 |
| Santal oriental | 30 |
| Coumarin | 25 |
| Musk ambrette | 10 |
| Musk ketone | 50 |
| Orange blossoms absolute, at 10% * | 15 |
| Jasmine absolute | 10 |
| Rose absolute | 20 |
| Undecalactone at 10% * | 10 |
| Vanillin at 10% * | 5 |
| Total | 990 |

* in diethyl phthalate

By adding to 990 g. of this blend 10 g. of cis-1,7,7-trimethylbicyclo[4.4.0]decan-3-one, the composition obtained had a pleasant amber and woody note which had a very natural touch.

+ in diethyl phthalate

EXAMPLE 3

Preparation of cis- and trans-1,7,7-trimethylbicyclo[4.4.0]decan-3-ones a. 6,10-Dimethyl-1,5,9-undecatriene Degreased magnesium turnings (84 g., 3.5 mole) were suspended in absolute ether (100 ml.). The Mg was activated with one crystal of iodine. In the course of about 3 hours, 300 g. (1.75 mole) of geranyl chloride, then 268 g. (3.5 mole) of allyl chloride in 800 ml. of ether were added dropwise. The mixture was boiled for 4 hours, then it was cooled and poured into a solution of 200 g. of NH$_4$Cl in 1 liter of ice water. The solution was extracted with ether. The extracts were treated as usual, after concentration, they gave 384 g. of crude 6,10-dimethyl-1,5,9-undecatriene which was used without further purification.

b. 1,7,7-Trimethylbicyclo[4.4.0]decan-3-ol

At 50° in the course of about 1½ hours, 384 g. of the triene prepared according to paragraph a.) above, were added dropwise to a mixture of 98% formic acid (2.7 kg.), concentrated H$_2$SO$_4$ (270 g.) and dioxan (1000 ml.). After stirring for 3 hours at 60°, the mixture was cooled and poured onto ice. It was extracted with ether. The extracts were neutralised with 10% aqueous Na$_2$CO$_3$, then they were washed with H$_2$O up to neutrality. The extract was dried as usual and concentrated. The residue (430 g.) was stirred for 4 hours at reflux temperature with a mixture of KOH (140 g.), H$_2$O (140 ml.) and methanol (1500 ml.). The methanol was removed under reduced pressure and the residue extracted with ether. The extract was neutralised, washed and dried as usual. The extract was concentrated and the residue (350 g.) was distilled under vacuum, b.p. 114°–125°/0.001 Torr, and gave the desired carbinol, m.p. 53°–54°.

c. Oxidation of 1,7,7-trimethylbicyclo[4.4.0]decan-3-ol

At 40°–45°, in the course of about 2 hours, a solution of $CrO_3$ (0.53 mole) in 200 ml. of water was added dropwise into a solution of 105 g. (0.53 mole) of the carbinol prepared according to the description of paragraph (b) above, in 800 ml of glacial acetic acid. The mixture was heated 4 hours at 70°. After cooling it was extracted with ether and the extract treated as usual. After concentration, 95 g. of a crude mixture of cis- and trans-1,7,7-trimethylbicyclo[4.4.0]decan-3-ones (approximately 1 : 1) was obtained. The crude product was recrystallised twice in hexane to give 46.5 g. of the pure cis-isomer, m.p. 46°–47°. IR spectrum (liquid phase): 965, 1215, 1450, 1705, 2940 $cm^{-1}$; NMR spectrum ($CCl_4$): 0.86 (6H, s), 0.96 (3H, s), 1.43 (8H, m), 1.95 (2H), 2.23 (2H, m) ppm ($\delta$).

The mother-liquors remaining from the above crystallisation were concentrated and the residue containing mainly the trans-isomer was purified by preparative vapour phase chromatography on a 2.5 m. 'Carbowax 20M' column, at 150° with a He flow of 40 ml./min. NMR spectrum ($CCl_4$): 0.87 (6H, s), 1.13 (3H, s), 1.5 (8H, m), 2.2 (4H, m) ppm ($\delta$).

EXAMPLE 4

Preparation of 1,7,7-trimethylbicyclo[4.4.0]decan-3-one

A mixture of 19.6 g. of 1,7,7-trimethylbicyclo[4.4.0]decan-3-ol, prepared according to the description of Example 1, paragraph (b) 72 g. of methylethylketone, 50 ml. of toluene, 10.5 g. of aluminium isopropoxide and 2 g. of aluminum chloride was heated to the boil for 6 hours. After cooling the mixture was stirred with 200 ml. of 10% $H_2SO_4$ and extracted with toluene. The extract was treated as usual and gave by distillation 8.2 g. of the bicycloketone, b.p. 85°–90°/0.001 Torr.

EXAMPLE 5

Preparation of 1,7,7-trimethylbicyclo[4.4.0]decan-3-one a. 6,10-Dimethyl-1,5,9-undecatriene Magnesium turnings (51 g., 2.1 mole) were suspended in 1700 ml. of ether and activated with a crystal of iodine. Allyl chloride (153 g., 2.0 mole) in 200 ml. of ether was added dropwise so as to maintain the mixture at reflux temperature throughout the addition. The mixture was refluxed for an additional 2 hours, then a solution of technical 82% pure geranyl chloride (210 g., 1.05 mole) in 200 ml. of ether was added dropwise at reflux temperature. The mixture was stirred for 2 hours at room temperature, then it was cooled down to 10° and slightly acidified with 20% aqueous acetic acid. The mixture was extracted with ether. The extracts were neutralised with 10% NaOH, washed with water, dried as usual and concentrated. The residue gave 217 g. of crude triene as a light yellow liquid the purity of which was 80% according to vapour phase chromatography; it was used without further purification.

b. 1,7,7-Trimethylbicyclo[4.4.0]decan-3-ol 6,10-Dimethyl-1,5,9-undecatriene (500 g.) prepared as described under (a) above was added dropwise at 30°–35° into a mixture of acetic acid (1 kg.) and conc. $H_2SO_4$ (165 g.). The reaction evolved much heat and the addition took 4 hours. The reaction mixture was stirred at 40° for 3 more hours, then 3 to 5 liters of ice water were added with violent stirring. The mixture was extracted twice with petroleum ether (b.p. 80°–100°). The extracts were neutralised with 10% NaOH and washed with $H_2O$. The moisture was removed by azeotropic distillation with the solvent and further concentration gave 562 g. of crude carbinyl acetate. Amyl alcohol (1124 g.) and KOH (199 g., 3.54 mole) were added to the acetate and the mixture was refluxed for 4½ hours. After cooling, the mixture was stirred with 10 liters of $H_2O$ and the alcohol layer was separated. After the usual treatment, distillation of the residue gave 246 g. of 1,7,7-trimethylbicyclo[4.4.0]decan-3-ol, b.p. 95°–127°/0.025 – 0.08 Torr.

c. Oxidation of 1,7,7-trimethylbicyclo[4.4.0]decan-3-ol

The carbinol prepared as described above in paragraph (b) (246 g.) was dissolved in 2.5 kg. of acetone purified according to usual means. 'Jones' oxidising mixture (642 g.), prepared according to J. Chem. Soc. 39 (1946), was added dropwise with cooling so as to maintain the temperature at 23°–25°. The mixture was left aside for 2 hours, then it was stirred with 1.5 liter of water and 500 ml. of petroleum-ether (b.p. 80°–100°). The mixture was allowed to stand overnight, then it was extracted twice with petroleum-ether. The combined extracts were treated as usual and gave 220 g. of crude bicycloketone. The latter was distilled to give 107.6 g., b.p. 77°–85°/0.015 – 0.025 Torr, of the mixture of cis- and trans-isomers. The said mixture was used directly as an ingredient in perfumery.

EXAMPLE 6

Preparation of the acetate of 1,7,7-trimethylbicyclo[4.4.0]decan-3-ol

The crude carbinyl acetate prepared according to the description of Example 5, paragraph (b), instead of being saponified was fractionated to give the pure ester in 87% yield, b.p. 90°–91°/0.01 Torr.

| Analysis: | Calc. for $C_{15}H_{26}O_2$ | C 75.58% H 11.00% |
|---|---|---|
| | Found | C 75.77% H 11.09% |

NMR spectrum ($CCl_4$): 0.80 (3H, s), 0.88 (3H, s), 1.00 (3H, s), 1.1 – 1.8 (12H, wide multiplet), 1.90 (3H, s), 4.80 (1H, wide band).

EXAMPLE 7

Preparation of 1,7,7-trimethylbicyclo[4.4.0]decyl-(3) acetate 22 g. of 1,7,7-trimethylbicyclo[4.4.0]decan-3-ol were heated 'hours at 90° with 15 g. of acetic anhydride and 15 g. of pyridine. The mixture was extracted with ether and, after the usual treatment, 23 g. of pure 1,7,7-trimethylbicyclo[4.4.0]decyl-(3) acetate, b.p. 90°–91°/0.01 Torr, were obtained.

| Analysis: | Calc. for $C_{15}H_{26}O_2$ | C 75.58% H 11.00% |
|---|---|---|
| | Found | C 75.77% H 11.09% |

EXAMPLE 8

When, in Example 7, acetic anhydride was replaced by an equivalent amount of propionic, butyric and acrylic anhydride, the corresponding esters were obtained in comparable yields. The table below summerises the results obtained with the said anhydrides:

| Anhydride | Esters (b.p.) |
|---|---|
| propionic | 98–102°/0.02 Torr |
| butyric | 113–117° 0.05 Torr |
| acrylic | 85–88°/0.01 Torr |

EXAMPLE 9

A perfume composition of the woody and amber-like type was prepared by mixing the following ingredients:

| Ingredients | Parts by weight |
|---|---|
| Phenylethanol | 155 |
| Styrax resinoid at 50% * | 215 |
| Heliotropin | 85 |
| Citronellol | 50 |
| Vanillin | 50 |
| Musk ketone | 40 |
| Patchouli | 25 |
| Synthetic civet at 10% * | 50 |
| Benzyl acetate | 280 |
| Total | 950 |

* in diethyl phthalate

The addition of 50 g. of 1,7,7-trimethylbicyclo[4.4.0]decyl-(3) acetate to 950 g. of the above mixture resulted in a perfume composition having more richness and roundness.

What is claimed is:

1. Compounds having the formula

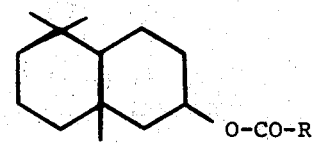

wherein R represents hydrogen, or an unsubstituted linear or branched alkyl having 1 to 6 carbon atoms, or an unsubstituted linear or branched alkenyl comprising 2 to 6 carbon atoms.

2. An ester selected from the group consisting of the formate, acetate, propionate, butyrate, and acrylate of 1,7,7-trimethylbicyclo (4.4.0)decan-3-ol.

* * * * *

UNITED STATES PATENT AND TRADEMARK OFFICE
CERTIFICATE OF CORRECTION

PATENT NO. : 3,989,739
DATED : November 2, 1976
INVENTOR(S) : Paul A. Stadler et al.

It is certified that error appears in the above-identified patent and that said Letters Patent are hereby corrected as shown below:

Column 5, line 43, "Musk ketone 60" should read
--Musk ketone 60--.

Column 8, line 58, "'hours" should read --2 hours--.

Signed and Sealed this

Fifteenth Day of March 1977

[SEAL]

Attest:

RUTH C. MASON
Attesting Officer

C. MARSHALL DANN
Commissioner of Patents and Trademarks